Figure 1:
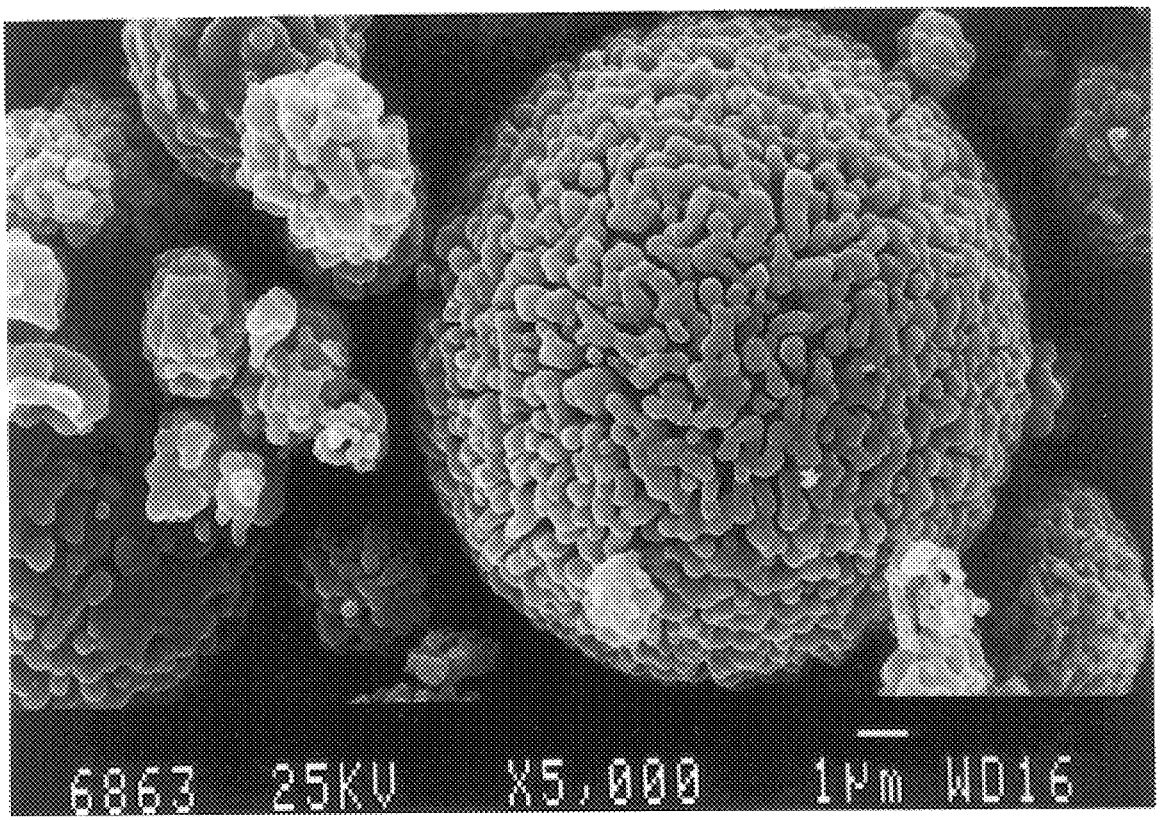

United States Patent [19]
Görge et al.

[11] Patent Number: 6,096,424
[45] Date of Patent: Aug. 1, 2000

[54] COBALT(II) OXIDE CONTAINING COBALT METAL, A PROCESS FOR PRODUCING IT AND ITS USE

[75] Inventors: Astrid Görge; Katrin Plaga, both of Goslar; Armin Olbrich, Seesen, all of Germany

[73] Assignee: H. C. Starck, GmbH & Co KG, Goslar, Germany

[21] Appl. No.: 09/233,812

[22] Filed: Dec. 12, 1998

Related U.S. Application Data

[62] Division of application No. 08/875,438, Jul. 9, 1997, Pat. No. 5,972,306.

[30] Foreign Application Priority Data

Feb. 10, 1995 [DE] Germany .......................... 195 04 320

[51] Int. Cl.⁷ ...................................................... B32B 5/16
[52] U.S. Cl. ........................... 428/403; 423/592; 423/594
[58] Field of Search ..................................... 428/403, 548, 428/570; 423/592, 594; 429/218

[56] References Cited

U.S. PATENT DOCUMENTS 5,032,475  7/1991  Hasebe et al. .
5,053,292  10/1991  Hasebe et al. .

FOREIGN PATENT DOCUMENTS 0 353 837  2/1990  European Pat. Off. ......... H01M 4/52
0 353 284  1/1993  European Pat. Off. ....... H01M 02/52

OTHER PUBLICATIONS

I. Matsumoto et al., Ni–Fe Battery, Abstract No. 10, 162d ECS Fall Meeting, Detroit, p. 18. (1982).

*Primary Examiner*—Hoa T. Le
*Attorney, Agent, or Firm*—Perkins, Smith & Cohen,LLP

[57] ABSTRACT

The present invention relates to cobalt(II) oxide containing metallic cobalt, to a process for producing it and to its use.

5 Claims, 3 Drawing Sheets

COBALT(II) OXIDE CONTAINING COBALT METAL, A PROCESS FOR PRODUCING IT AND ITS USE

The present application is a divisional application of prior application Ser. No. 08/875,438, filed Jul. 9, 1997, now U.S. Pat. No. 5,972,306.

The present invention relates to cobalt(II) oxide containing metallic cobalt, to a process for producing it and to its use.

Cobalt(II) oxide is used in admixture with metallic cobalt as an additive in the positive paste material of rechargeable alkaline Ni batteries based on Ni/Cd or Ni/NiH. For this purpose $Ni(OH)_2$ is processed with the Co(II) oxide-metal mixture and auxiliary materials to form pastes which are subsequently incorporated in an electrically conductive electrode support. The electrodes produced by this route are further processed by drying and/or sintering in order thus to produce batteries of various designs.

Thus for the production of round button cells, for example, the electrochemically active electrode constituents are compacted together with auxiliary materials, predominantly graphite or nickel powder, to form tablets of various sizes. The content of cobalt in the electrode compositions is between 2 and 10% by weight in this application.

According to EP-A 353 837, the main effect of cobalt metal is due to the fact that during the first charging cycles (forming cycles) the cobalt metal first is oxidised, corresponding to its potential, to divalent cobalt, and is thus able to dissolve in alkaline electrolytes. The $Co^{2+}$ ions which are thus obtained and those which may already be present then diffuse towards the surface of the nickel hydroxide. On further charging of the battery, they are oxidised here to $Co^{3+}$ ions in the form of CoO(OH). This in turn is formed as a layer on the surface of the nickel hydroxide particles and gives rise to the electric conductivity of the electrode material during the following charging and discharging cycles.

However, $Co^{2+}$ ions can also enter the layer lattice of the nickel hydroxide and can modify the properties of the hydroxide there so that a higher charging efficiency of the electrode material is obtained. In addition to the properties which have already been mentioned, the cobalt used in the electrode paste material can act as a safety reserve if discharging is too intensive. In the course of this procedure, $Co^{2+}$ ions are electrochemically reduced again and thus prevent the evolution of hydrogen. Cobalt compounds with the aforementioned properties are also disclosed in U.S. Patent Specifications U.S. Pat. Nos. 5,032,475 and 5,053,292, and in European Patent Application EP-A 523 284.

Only up to about 50% of the cobalt in the electrode can be utilised for the charging and discharging cycles on electrochemical oxidation, since the predominant fraction of the cobalt is coated with a stable oxide layer. This protective layer in turn prevents the formation of $Co^{2+}$ ions which are necessary for the activation of the electrode, as mentioned above. In order to circumvent this difficulty, soluble cobalt compounds such as cobalt hydroxide or monoxide have hitherto been incorporated in the electrode paste material. The effect of this has been that $Co^{2+}$ ions are present in dissolved form in the electrolyte even before electrochemical forming, and can already separate out at the surface of the nickel hydroxide (Matsumo et al.: The 162nd ECS Fall Meeting Detroit, 18 (1982).

According to this prior art, the Co(II) oxide used for the purposes of application described above is produced commercially by the thermal decomposition of cobalt carbonate, cobalt hydroxide or higher oxides of cobalt. In accordance with thermodynamic equilibrium considerations, however, these always contain an excess of oxygen and thus have residual contents of Co(III).

However, slight traces of Co(III) in Co(II) oxide catalyse the oxidation of divalent cobalt to trivalent cobalt. The latter does not form compounds which are soluble in the electrolyte, however, so that the formation of the conductive layer according to the mechanism described above is not possible. The result of this is that a high utilisability of the electrode can only be obtained if the Co(III) content of the starting material is as low as possible.

The object of the present invention is therefore to provide a Co(II) oxide containing cobalt metal which does not have the disadvantages described above.

It has now proved possible to obtain corresponding Co(II) oxides by a process for producing Co(II) oxide containing metallic cobalt, wherein crystallised basic cobalt compounds of general formula

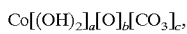

where
the sum of a+b+c is $\geq 1 \leq 1.5$,
are reacted with aqueous and/or alcoholic solutions of an organic compound containing at least one carboxyl group and the solids thus obtained are separated from the suspension and calcined. The present invention relates to such a process.

Carboxylic acids can preferably be used as the organic compound containing at least one carboxyl group in the process according to the invention. In this respect, particularly suitable substances from the group comprising carboxylic acids are linear or branched, saturated or unsaturated monocarboxylic acids having a number of C atoms from 1 to 9, and/or linear or branched, saturated or unsaturated polycarboxylic acids having a number of C atoms from 2 to 10, and/or cyclic or heterocyclic, saturated or unsaturated mono- and polycarboxylic acids having a number of C atoms from 4 to 14, and/or linear or branched, saturated or unsaturated mono- and polyhydroxy carboxylic acids having a number of C atoms from 2 to 7, and/or aromatic hydroxycarboxylic acids having a number of C atoms from 7 to 11, and/or cyclic or aliphatic, saturated or unsaturated ketocarboxylic acids having a number of C atoms from 2 to 14.

Adipic acid, succinic acid, glutaric acid, glyoxylic acid, maleic acid, malonic acid, lactic acid, oxalic acid, phthalic acids, mucic acid, sorbic acid, racemic acid, versatic acid, tartaric acid and/or citric acid can be used just as advantageously.

In a further advantageous embodiment of the process according to the invention, the carboxylic acids may also be used in partially esterified form, as long as they still contain at least one active carboxyl group.

Crystallised basic cobalt compounds in the sense of this invention have the formula

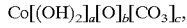

where the sum of a+b+c is $\geq 1 \leq 1.5$. The values of a, b and c may each be any values between 0 and 1.5. They can thus be used both as pure crystals and as mixed crystals, wherein the cobalt may be present in oxidation states between 2 and 3. Compounds which are particularly suitable are those having particle sizes in the region of 0.5 µm, preferably 2 to 20 µm. They are most preferably present within a narrow particle size distribution.

The external shape of the crystallised basic cobalt compounds also determines the shape of the final products according to the invention. Those exhibiting a spherical morphology are most preferably used.

The calcination step which completes the process is advantageously effected under an inert gas atmosphere at temperatures between 200 and 1000° C., preferably 500 to 800° C.

Depending on the control of the process, the process according to the invention permits both a selective conversion of the external surface of the particles, and a conversion of the internal surface in addition.

Figure 2:
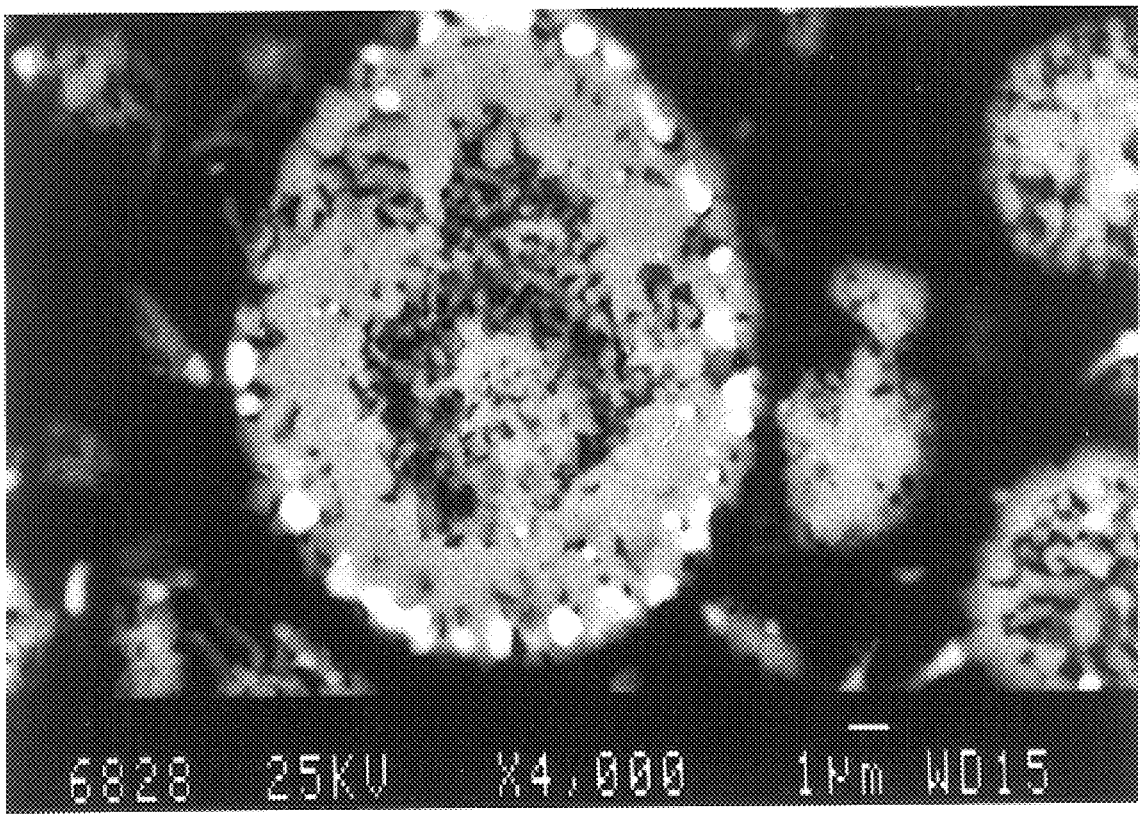

In order to obtain Co(II) oxide wherein the metallic cobalt is situated predominantly on the external surface of the Co(II) oxide, the reaction according to the invention is conducted within a temperature range from 50 to 100° C., preferably 70 to 90° C. This invention relates to correspondingly obtainable Co(II) oxides. A scanning electron microscope photograph of microsections of corresponding Co(II) oxides is illustrated in FIG. 2. Metallic cobalt particles in the submicron range, which are concentrated in discrete form in the external surface, are typical of these oxides.

This invention also relates to Co(II) oxides in which the metallic cobalt exists in an concentrated state in both the internal and in the external surface. A photograph of a corresponding Co(II) oxide is likewise illustrated as a microsection in FIG. 3. It can be obtained by the process according to the invention, wherein the reaction is firstly conducted for 0.1 to 3 hours, preferably 0.5 to 1.5 hours, at room temperature, and is subsequently conducted for 0.1 to 3 hours at 50 to 100° C., preferably 70 to 90° C. A three-dimensional network of finely divided metallic cobalt is typical of these Co(II) oxides.

The content of metallic cobalt in the Co(II) oxide according to the invention can be adjusted to any desired ratio by means of the ratio of the corresponding reduction equivalents. Contents of metallic cobalt from 2 to 50% by weight, most preferably 3 to 20% by weight, are preferred.

The Co(II) oxides according to the invention are characterised by a high resistance to atmospheric oxygen. Another merit of the material, for example, is its high flowability when spherical particles are used, since the habit of the materials are maintained during the entire course of the reaction.

Another advantage is manifested in that, compared with materials produced according to the prior art, the metallic and oxide fractions cannot segregate, which facilitates uniform processing of the cobalt in the paste preparation operation which is necessary for the production of electrodes.

This invention also relates to the use of the Co(II) oxides according to the invention as an electrode material in electrochemical secondary cells.

The invention is explained below by means of examples, without being seen as being restricted thereto.

EXAMPLE 1
(External Coating)

200 g of spherical basic cobalt carbonate, produced by the reaction of $CoC_{12}$ with $Na_2CO_3$, were slurried in 1.5 liters of water and this suspension was heated to 85° C. with stirring. Metered additions of 100 g of solid tartaric acid were made uniformly to this suspension over 30 minutes, the temperature being maintained at 85° C. The reaction mixture was subsequently stirred for 15 minutes at T=85° C. and then filtered hot. The filter cake was subsequently washed with 500 ml of water and dried to constant weight at T=70° C.

260 g of basic cobalt tartrate/carbonate were obtained as an intermediate product.

100 g of this product were calcined in a quartz boat at T=700° C. for 3 hours under argon.

67 g of Co(II) oxide containing cobalt metal, which had a cobalt content of 79.72%, were obtained as the calcination product.

EXAMPLE 2
(External Coating)

200 g of spherical basic cobalt carbonate, produced as in Example 1, were slurried in 1000 ml of methanol. 20 g of citric acid monohydrate—dissolved in 50 ml of methanol—were added thereto with stirring. The suspension was subsequently heated for 4 hours under reflux, filtered, and washed with 1000 ml of methanol. The filter cake was dried to constant weight at T=70° C.

212 g of basic cobalt citrate/carbonate were obtained as an intermediate product, which was calcined at T=700° C. for 2 hours in an argon atmosphere. The Co(II) oxide containing cobalt metal which was obtained (27 g) had a cobalt content of 79.3%.

A correspondingly produced powder is illustrated in FIG. 1 (magnification 5000x).

EXAMPLES 3 to 6
(External Coating)

200 g of spherical basic cobalt carbonate, produced as described in Example 1, were suspended in water and heated to T=80° C. This was followed by the addition of oxalic acid in the amounts given in Table 1. After the reaction was complete, the suspension was stirred for 1 hour, filtered, and dried to constant weight at T=70° C.

The materials obtained by this route were subsequently subjected to calcination at 700° C. under an inert gas.

TABLE 1

| Starting material: | spherical Co carbonate Co content: 54.5 % amount originally weighed in: 200 g | |
| --- | --- | --- |
| Example No. | Amount of oxalic acid weighed in | Cobalt content in final product |
| 3 | 46 g | 81.5% |
| 4 | 70 g | 83.1% |
| 5 | 81 g | 83.8% |
| 6 | 93 g | 85.0% |

A powder produced according to Example 5 is illustrated in the form of a microsection in FIG. 2 (magnification 4000x).

EXAMPLE 7
(External and Internal Coating)

200 g of spherical basic cobalt carbonate, produced as described in Example 1, were slurried in 1.5 liters of water and 100 g of tartaric acid were added. The suspension was stirred for 1 hour at room temperature and subsequently heated to 53° C. for 2.5 hours. It was subsequently filtered and washed with 500 ml of water. After drying to constant weight the residue on the filter gave 261 g of basic cobalt tartrate/carbonate as an intermediate product.

This was calcined at T=700° C. for 3 hours under an argon atmosphere. 137 g of Co(II) oxide containing cobalt metal, which had a cobalt content of 91.4%, were obtained as the calcination product.

EXAMPLE 8
(External and Internal Coating)

200 g of spherical basic cobalt(II, III) hydroxide-oxide with a Co content of 49% by weight of cobalt were slurried with 1.5 liters of water, and 15 g of solid tartaric acid were added. The suspension formed was stirred for 1.5 hours at room temperature and subsequently heated to 70° C. for 2 hours. Thereafter it was filtered, washed, and dried to constant weight. The 212 g of basic cobalt tartrate/(II, III) hydroxide-oxide obtained from the reaction was subjected to calcination at T=700° C. for 3 hours under an inert gas.

117 g of Co(II) oxide containing cobalt, which had a cobalt content of 80.8%, were obtained as the product.

Figure 3:
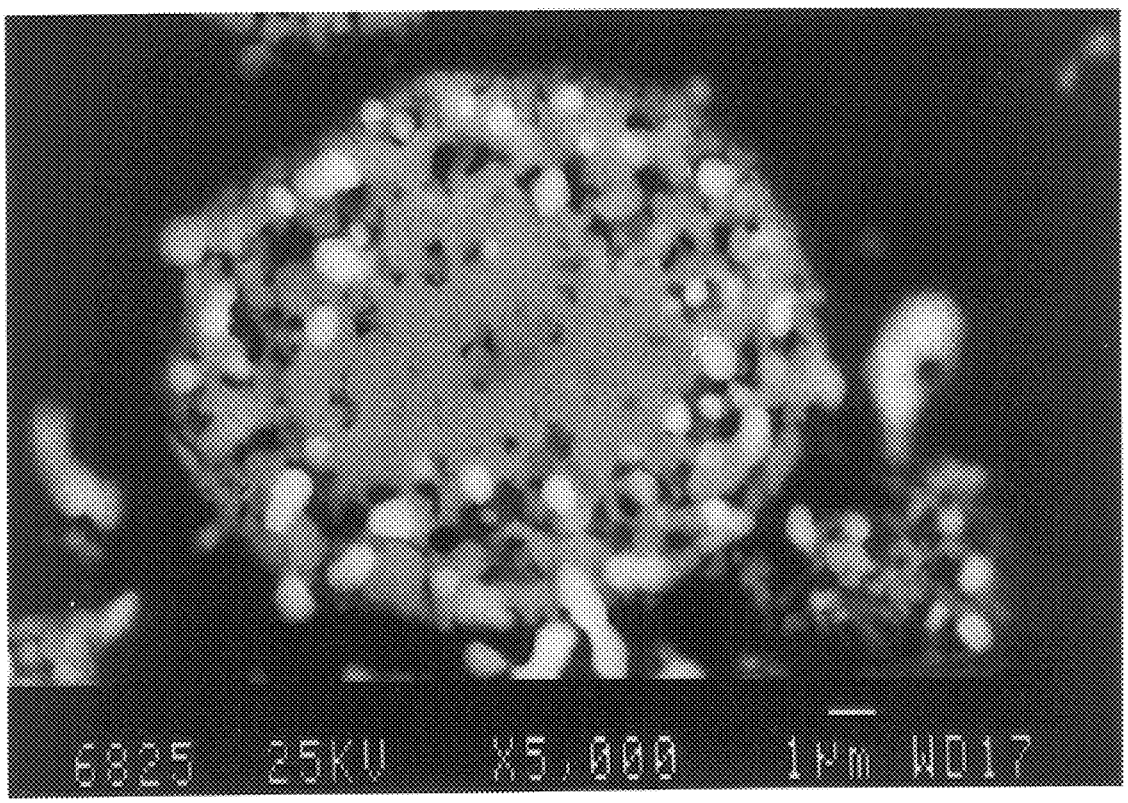

A correspondingly produced powder is illustrated in the form of a microsection in FIG. 3 (magnification 5000×).

What is claimed is:

1. Co(II) oxide product made by a process comprising:
   (1) reacting crystallized basic cobalt compounds of the general formula $Co[(OH)_2]_a[O]_b[CO_3]_c$, where $1 \leq a+b+c \leq 1.5$, with aqueous and/or alcoholic solutions of an organic compound containing at least one carboxyl group;
   (2) separating solids from the suspension which results from the reaction;
   (3) calcining the resulting solids at 500–800° C. whereby Co metal forms on the surface of the Co(II) oxide;
   wherein the crystallized basic cobalt compounds have particles sizes within a range of 2 to 20 μm, and wherein the reaction is initially conducted at room temperature for 0.5 to 1.5 hours and then at 70 to 90° C. to completion.

2. Co(II) oxide product made by a process comprising:
   (1) reacting crystallized basic cobalt compounds of the general formula $Co[(OH)_2]_a[O]_b[CO_3]_c$, where $1 \leq a+b+c \leq 1.5$, with aqueous and/or alcoholic solutions of an organic compound containing at least one carboxyl group;
   (2) separating solids from the suspension which results from the reaction;
   (3) calcining the resulting solids wherein said solids comprise Co(II) oxide particles with metallic cobalt therein;
   wherein the organic compound containing at least one carboxyl group is a carboxylic acid selected from the group consisting of:
   (a) linear or branched, saturated or unsaturated monocarboxylic acids having a number of carbon atoms from 1 to 9;
   (b) linear or branched, saturated or unsaturated polycarboxylic acids having a number of carbon atoms from 2 to 20;
   (c) cyclic or heterocyclic, saturated or unsaturated mono- and poly-carboxylic acids having a number of carbon atoms from 4 to 14;
   (d) linear or branched, saturated or unsaturated mono- and poly-hydroxycarboxylic acids having a number of carbon atoms from 2 to 7;
   (e) aromatic hydroxycarboxylic acids having a number of carbon atoms from 7 to 11; and
   (f) cyclic or aliphatic, saturated or unsaturated ketocarboxylic acids having a number of carbon atoms from 2 to 14.

3. Co(II) oxide product according to either of claims 1 or 2, containing metallic cobalt, wherein the metallic cobalt is predominantly present on the external surface of the Co(II) oxide.

4. Co(II) oxide product according to either of claims 1 or 2 containing metallic cobalt, wherein the metallic cobalt is present both on the external and on the internal surface of the Co(II) oxide.

5. An electrode of a secondary energy storage cell comprising the Co(II) oxide product of either of claims 1 or 2.

* * * * *